United States Patent [19]

Coupland et al.

[11] Patent Number: 5,194,448
[45] Date of Patent: Mar. 16, 1993

[54] USE OF NERVONIC ACID AND LONG CHAIN FATTY ACIDS FOR THE TREATMENT OF DEMYELINATING DISORDERS

[75] Inventors: Keith Coupland, Hotham; Nigel A. Langley, Wilbersoss, both of Great Britain

[73] Assignee: Croda International PLC, North Humberside, Great Britain

[21] Appl. No.: 730,916

[22] PCT Filed: Nov. 30, 1990

[86] PCT No.: PCT/GB90/01870
§ 371 Date: Aug. 6, 1991
§ 102(e) Date: Aug. 6, 1991

[87] PCT Pub. No.: WO91/07955
PCT Pub. Date: Jun. 13, 1991

[30] Foreign Application Priority Data

Nov. 30, 1989 [GB] United Kingdom ................ 8927109
Jul. 30, 1990 [GB] United Kingdom ................ 9016660

[51] Int. Cl.$^5$ ............................................. A61K 31/20
[52] U.S. Cl. ..................................... 514/558; 514/930
[58] Field of Search ...................... 424/195.1; 514/558, 514/930

[56] References Cited

U.S. PATENT DOCUMENTS 4,505,933  3/1985  Horrmann ........................... 514/693

FOREIGN PATENT DOCUMENTS 2218334  11/1989  United Kingdom .

OTHER PUBLICATIONS

Holm et al., PNAS 1989, 86:4720–4724.
B Gerstl, et al., Z. NBeurol. 202:104–120 1972.

*Primary Examiner*—John W. Rollins
*Attorney, Agent, or Firm*—Watson, Cole, Grindle & Watson

[57] ABSTRACT

Composition containing nervonic acid (cis-tetracos-15-enoic acid) in a physiologically acceptable form are useful in the treatment of demyelinating disease, such as multiple sclerosis. Additional long chain fatty acids of chain length C16 to C26, especially erucic acid, or their esters, may be included in such compositions.

14 Claims, No Drawings

USE OF NERVONIC ACID AND LONG CHAIN FATTY ACIDS FOR THE TREATMENT OF DEMYELINATING DISORDERS

This invention is concerned with pharmaceutical compositions containing long chain fatty acids such as nervonic acid, or derivatives thereof, for the treatment of demyelinating diseases such as multiple sclerosis.

Multiple sclerosis (MS) is a disease affecting the mature central nervous system (CNS). The disease is characterised by successive periods of CNS demyelination followed by periods of remission. Although the aetiology of MS is not fully understood a number of factors appear to be important including a genetic predisposition, viral infection and an auto immune response to some antigen resulting in demyelination of the CNS particularly brain, optic nerve and spinal cord.

Regardless of the causes of MS, the pattern of demyelination and remyelination (remission) involves both loss of and reassimilation of myelin components. Since myelin comprises about 60% of its dry weight as lipid, the important lipid components, the fatty acids, have received considerable attention over the years, in particular the long chain fatty acids, since they are the most abundant of fatty acids in many important complex lipids. Long chain fatty acids in the context of this invention are defined as those mono-carboxylic acids having a carbon chain length greater than C22. The complex lipids in the context of this invention include gangliosides (particularly Ganglioside $G_7$ or $G_{M4}$), cerebrosides, sulphatides and sphingomyelin. These lipids contain significant amounts of long chain fatty acids (particularly nervonic acid-cis-tetracos-15-enoic acid) in their structures. Typical compositions of normal myelin are tabulated below:

TABLE 1

| | Long Chain Fatty Acids in Myelin Lipids | | | |
|---|---|---|---|---|
| Fatty Acid* | Ganglioside $G_7(G_{M4})$** | Cerebroside** | Sulphatide** | Sphingomyelin*** |
| C24:1 | 24.1 | 45.7 | 48.0 | 35.0 |
| C24:0 | 11.1 | 15.8 | 14.3 | — |
| C25:1 | 5.0 | 7.8 | 10.2 | 2.3 |
| C25:0 | 1.8 | 2.3 | 3.4 | — |
| C26:1 | 4.1 | 4.5 | 9.1 | 1.0 |
| C26:0 | 0.8 | 0.3 | 1.1 | — |

*The total number of carbon atoms: number of double bonds
**Derived from human purified myelin (see Ledeen. R. W., et al J. Neurochem., 21 829-839, 1973).
***Derived from human white brain matter (see Gerstl, B., et al Z. Neurol., 202 104-120, 1972).

Destruction of myelin during active MS results in significant loss of these myelin components. Additionally, their replacement requires the availability of their specific component fatty acids. This can arise by two distinct routes, namely in-vivo synthesis (the more important route) and exogenously from the diet. Long chain fatty acids are rare trace components in most modern diets and in-vivo synthesis is not efficient and may be impaired in MS. Several workers have shown that there is a significant depletion of total lipid in MS tissue (brain, spinal cord). More significantly, perhaps, is the absence of specific gangliosides (Ganglioside $G_7$ or $G_{M4}$) in MS white brain matter and demyelinated plaque (see Yu, R. K. et al, J. Neurochem., 23 169–174, 1974).

Myelin destruction not only depletes CNS tissue of vital lipids but also releases myelin basic protein (MBP). MBP is known to be antigenic to myelin and also induces experimental allergic encephalomyelitis (EAE) when injected into laboratory animals. EAE has some neuropathological features in common with MS and is widely used as an animal model for the diseases. However, when MBP is incubated with Ganglioside $G_7$ ($G_{M4}$) prior to injection it significantly reduces the encephalogenic potential of the MBP in guinea pig. (See Mullin, B. R., et al Brain Research, 296 174–176, 1984).

We have now realised that the provision of a pharmacologically acceptable source of long chain fatty acids in MS patients would provide a pool of material vital to the assembly of myelin components for reassembly of the myelin sheath. Moreover the ready availability of these long chain fatty acids would enable the biosynthesis of important gangliosides, particularly Ganglioside $G_7$ ($G_{M4}$) which is known to inhibit the myelinogenic propensity of MBP. According to the present invention, therefore, there is provided a pharmaceutical composition comprising one or more long chain fatty acids, in a physiologically acceptable form, and a carrier or diluent therefor. Preferably, the compositions include nervonic acid as the, or one of the, fatty acids, e.g. in the form of an ester thereof.

Although the long chain fatty acids such as nervonic acid (cis-tetracos-15-enoic acid) are rare or insignificant in normal diets, they do exist in a small number of plants and micro-organisms. These include the seed oils of *Cardamine gracea, Heliphila longifola, Thlaspi perfoliatum, Tropaeolum speciosum, Lunaria biennis, Lunaria annua* and *Malania oleifera*; the moulds *Neocallismastix frontalis, Erysiphe graminis* and *Sphaerotheca humuli*; the bacterium *Pseudomonas atlantica*; the yeast *Saccharomyces cerevisiae* and the marine diatom *Nitzschia cylindrus*.

A preferred source is the seed oil of plants known to contain significant amounts, i.e. greater than 10%, of nervonic acid in the triglyceride lipid. Clearly other sources containing less than 10% are of lower value since additional steps would have to be taken to concentrate the active components. Of particular value is the seed oil of *Lunaria biennis* or *Lunaria annua* since they contain over 20% nervonic acid in the triglyceride. A detailed typical composition of the oil is shown in Table 2.

TABLE 2

| Fatty Acid Distribution in L.biennis Seed Oil* | | | |
|---|---|---|---|
| Fatty Acid | Name | Amount (%)** | Amount (%)**** |
| C16:0 | palmitic acid | 1.2 | 1.1 |
| C16:1 | oleopalmitic acid | 0.2 | 0.1 |
| C18:0 | stearic acid | 0.2 | 0.2 |
| C18:1 | oleic acid | 23.4 | 23.3 |
| C18:2 | linoleic acid | 4.8 | 5.4 |
| C18:3 | linolenic acid | 1.0 | 0.8 |
| C20:0 | eicosanoic acid | tr*** | —***** |
| C20:1 | eicosenoic acid | 1.6 | 0.5 |
| C22:0 | behenic acid | 0.2 | 0.2 |
| C22:1 | erucic acid | 45.3 | 45.1 |
| C22:2 | docosandienoic acid | 0.1 | 0.2 |
| C24:0 | tetracosanoic acid | 0.2 | 0.1 |
| C24:1 | nervonic acid | 21.8 | 22.8 |
| | | 100.00 | 100.00 |

*Analysed by gas chromatography
**The triglycerides ester converted to the corresponding methyl ester
***trace amount, usually less than 0.1%
****second determination on a different sample
*****not detected In addition to the various natural sources, examples of which are listed above, it is also possible to provide nervonic acid by a synthetic procedure. The starting point for such synthesis could be, for example, the readily available erucic acid (cis-docosa-13-enoic acid). A typical synthesis, but by no means the only possibility, has been described by Carrol, K. K. (see Canadian J. Chem., 35 757–760, 1957). This synthesis involves the conversion of erucic acid to its methyl ester by esterification with methanol, reduction to erucyl alcohol using lithium aluminium hydride, conversion of the alcohol to its alkyl bromide by reaction with phosphorous tribromide, reaction of the erucyl bromide with diethyl malonate and decarboxylation to yield nervonic acid. This synthesis has some advantages, particularly in the preparation of isotopically labelled nervonic acid, but suffers from the lengthy procedure and cost.

The various methods of extracting seed oils from the oil bearing seeds are well known to those skilled in the art (see "Baileys Industrial oil and Fat Products", ed. D. Swern, Vol. 2, pages 175 et seq. 4th edition, Pub. 1982, John Wiley & Sons Inc.). These methods include: dry rendering, wet rendering, batch pressing, continuous pressing, solvent extraction and extraction with supercritical gases such as carbon dioxide. In practice the most efficient processes involve continuous pressing or supercritical extraction with or without secondary solvent extraction of the oil seed cake.

Extracted oils free from solvent may also contain undesirable impurities which can detract from the value of the oil as a pharmaceutical. Undesirable impurities or contaminants may be removed by various refining processes. Refining is defined as any purifying treatment designed to remove free fatty acids, phosphatides, gums or other major impurities.

The oil may be further improved by bleaching and deodorisation. Bleaching is defined as any process designed to reduce the colour of the oil. Various methods are used and are well known to those skilled in the art. Deodorisation is defined as any process designed to remove trace contaminants that give rise to flavour and odour.

Bleaching and deodorisation are described in detail in "Baileys Industrial Oil & Fat Products" ed. D. Swern, Vol. 2, 4th edition, pages 253 et seq, Pub. 1982, John Wiley & Sons Inc.

A particularly valuable purification process which has the advantage of refining, bleaching and deodorisation in one step is by adsorption chromatography.

As can be seen from Table 2, natural oils contain a large number of component fatty acids in addition to the long chain fatty acids. If desired, the long chain fatty acids may be concentrated by selectively removing other components. Suitable methods include conversion of the triglyceride to the free fatty acid or lower alkyl ester, particularly their methyl or ethyl esters. Concentration may then be effectively performed by fractional distillation, crystallisation, solvent extraction, urea clathration or chromatography to yield nervonic acid rich fractions. In some cases, it may be desirable to use combinations of these techniques.

The compositions of the invention may comprise nervonic acid as the only therapeutically active substance. Alternatively one or more other active materials may be present.

A further embodiment of the invention involves the use of a functional derivative of the long chain fatty acids, in particular functional derivatives of nervonic acid. As used herein the term "functional derivative" is defined as any of those derivatives of long chain fatty acids herein defined, particularly nervonic acid, which contain the intact nervonyl acyl group. Examples of these functional derivatives include esters, particularly glyceride esters, ethyl esters and the like, salts such as sodium salts, potassium salts, calcium salts, amino acid salts and the like. The acids and their functionally active derivatives may be prepared synthetically by processes described heretofore. These processes involve, however, a number of stages and high cost. It is especially preferred, therefore, that the materials be obtained from naturally occurring seed oils or micro-organisms. Particularly preferred are seed oils such as those described heretofore and especially the seed oil of Lunaria family.

It is further preferred that the long chain fatty acids, particularly nervonic acid or functional derivatives thereof, are administered in a suitable pharmaceutically acceptable form. Many such forms are known and include oral administration of the oil itself, the free fatty acids or functional derivatives thereof. Additionally, the oil free fatty acids or functional derivatives may be administered as capsules, tablets or emulsions in water. Furthermore, the pharmaceutical composition may be administered where appropriate by injection, intravenous intubation or nasogastric intubation, for example.

It is understood that the amount of material administered is defined as the amount of active therapeutic material required to achieve the required pharmacological effect. In general, the required dosage rate for an adult will range from 0.01 g–50 g per day, especially in the range 0.1 g–10 g, and preferably 0.5 g–5 g per day, of the nervonic acid containing oil, functional derivative thereof or pure nervonic acid or functional derivative thereof.

As is well known MS is one of a group of demyelinating diseases including acute disseminated encephalomyelitis, Western Hurst disease, progressive multifocal leukoencephalopathy, idiopathic polyneuritis, diphtheric neuropathy, adrenoleukodystrophy (ALD) and adrenomyeloneuropathy. It is possible that one or more of these diseases could benefit from treatment with the nervonic acid containing preparations described above. The preferred compositions of the invention based on natural oils, particularly from the Lunaria plants all contain, in addition to nervonic acid, substantial quantities of erucic acid. Erucic acid and its derivatives are effective methods of reducing the concentration of accumulated toxic methabolites characteristic of ALD. Thus, these preferred compositions of the present invention can also be used for treating ALD. When used for this purpose, however, the oil should not contain any significant amounts of tetracosanoic acid or hexacosanoic acid. Removal of these components can be achieved by the methods well known to those skilled in the art and include the removal of all saturated fatty acids by urea clathration. Additionally when treating ALD it is often preferred to restrict the patients diet to exclude all dietary sources of undesirable fatty acids especially tetracosanoic acid and hexacosanoic acid. Rigorous restriction may, in some cases, also exclude fatty acids essential for growth, metabolism and health. Where this is the case the nervonic acid containing oils may be supplemented with suitable amounts of these fatty acids. These include gamma-linolenic acid, eicosapentaenoic acid and docosahexanenoic acid.

EXAMPLE 1

We described hereafter, by way of illustration only, the treatment of Honesty oil to obtain a concentrate of ethyl nervonate, and the preparation therefrom of purified glyceryl trinervonate which is a useful physiologically acceptable derivative of nervonic acid.

The typical composition of the crude oil is as follows:

| Fatty Acid | Amount (%) |
|---|---|
| C16:0 | 1.2 |
| C16:1 | 0.2 |
| C18:0 | 0.2 |
| C18:1 | 23.4 |
| C18:2 | 4.8 |
| C18:3 | 1.0 |
| C20:0 | Trace |
| C20:1 | 1.6 |
| C22:0 | 0.2 |
| C22:1 | 45.3 |
| C22:2 | 0.1 |
| C24:0 | 0.2 |
| C24:1 | 21.8 |

(A) Preparation of ethyl esters

Honesty oil is converted into its ethyl esters by reacting the oil (1 mol) with an excess of absolute alcohol (5 mol) in the presence of sodium ethoxide (0.01 mol) at 80° C. for 3 hours. The reaction mixture is then cooled to 30° C. and the lower glycerol layer is separated off. The product is washed three times with water at 80° C. and then dried under vacuum up to a temperature of 110° C.

| Fatty Acid Composition | |
|---|---|
| Fatty Acid | Amount (%) |
| C16:0 | 1.2 |
| C16:1 | 0.2 |
| C18:0 | 0.2 |
| C18:1 | 23.2 |
| C18:2 | 4.9 |
| C18:3 | 1.1 |
| C20:0 | Trace |
| C20:1 | 1.6 |
| C22:0 | 0.2 |
| C22:1 | 45.1 |
| C22:2 | 0.1 |
| C24:0 | 0.2 |
| C24:1 | 22.0 |

(B) Purification of Ethyl Ester—Removal of Saturated Fatty Acids

Saturated fatty acid ethyl esters are removed from the Honesty ethyl ester by refluxing with an excess of urea dissolved in absolute alcohol for 2 hours. On cooling with stirring over 14 hours to ambient temperature the saturated ethyl esters crystallise out as the urea-fatty acid inclusion compounds.

The solid inclusion compounds and excess urea are removed by filtration leaving an alcohol solution of unsaturated ethyl esters. This is concentrated by vacuum distillation to remove the solvent.

The crude "saturate free" ethyl esters are washed one, at 85°-90° C. with dilute aqueous potassium hydroxide, and washed again with two portions of hot water to remove any traces of soap and urea present in the crude product. The product is then dried under vacuum at a temperature of 100° C.

| Fatty Acid Composition | |
|---|---|
| Fatty Acid | Amount (%) |
| C16:0 | Trace |
| C16:1 | 0.4 |
| C18:0 | Trace |
| C18:1 | 23.5 |
| C18:2 | 5.0 |
| C18:3 | 1.2 |
| C20:0 | Trace |
| C20:1 | 1.7 |
| C22:0 | Trace |
| C22:1 | 45.4 |
| C22:2 | 0.2 |
| C24:0 | Trace |
| C24:1 | 22.6 |

(C) Enrichment of Ethyl nervonate (C24:1) by Fractional Distillation the "saturate free" ethyl esters are enriched in C24:1 by fractional distillation to give a residue containing 50–90% C24:1). The crude ethyl nervonate is then further distilled under vacuum.

| Fatty Acid Composition | |
|---|---|
| Fatty Acid | Amount (%) |
| C18:1 | Trace |
| C18:2 | Trace |
| C18:3 | Trace |
| C20:1 | 0.3 |
| C22:1 | 8.5 |
| C22:2 | 1.1 |
| C24:1 | 90.1 |

(D) Preparation of Glyceryl trinervonate (GTN)

GTN is prepared by reacting stoichiometric amounts of the enriched ethyl nervonate (90%) with glyceryl (BP) using sodium methoxide (0.03 mol) as catalyst.

The reaction is carried out in a stepwise manner by (a) adding 85% of the glycerol initially and reacting for 10 hours at 220° C. under vacuum. (b) adding a further 7% and reacting for 3 hours at 220° C. (c) adding a further 4% and reacting for 3 hours at 220° C. (d) adding the final 4% and reacting for 5 hours at 220° C. The total reaction time being 21 hours.

This gradual addition of the glycerol is necessary to maximise the conversion of the ethyl ester to the triglyceride and to minimise the formation of mono and diglycerides. After the reaction period has elapsed the crude triglyceride is cooled to 40° C.

(E) Chromatographic Purification of GTN

The crude GTN is dissolved in pure hexane and subjected to column chromatography using activated silicon dioxide as the absorbant.

The combined column eluate is isolated and distilled to remove hexane. The residue is then steam distilled under vacuum at 110° C. The GTM is filtered in vacuo at 70° C. to give a pale yellow liquid which solidifies on standing at ambient temperature.

| Fatty Acid Composition | |
|---|---|
| Fatty Acid | Amount (%) |
| C18:1 | Trace |
| C18:2 | Trace |
| C18:3 | Trace |

-continued

| Fatty Acid Composition | |
|---|---|
| Fatty Acid | Amount (%) |
| C20:1 | 0.3 |
| C22:1 | 8.4 |
| C22:2 | 1.1 |
| C24:1 | 90.2 |

EXAMPLE 2

One preferred composition of the invention comprises the glyceryl trinervonate oil (described in Example 1) as the active ingredient. The oil can be administered orally to patients either as such or in encapsulated form. Suitable capsules are gelating capsules containing about 1 g of oil. The dose will depend on the patient's circumstances but we believe it will normally be from 5 to 10 g per day per adult. The gelatin of the capsules would, of course, constitute a carbohydrate and protein source for the patient.

The oil can also be prepared as an emulsion for oral administration if desired.

We claim:

1. A pharmaceutical composition for use in the treatment of demyelinating diseases such as multiple sclerosis by oral ingestion, said composition consisting essentially of nervonic acid (cis-tetracos-15-enoic acid) in physiologically acceptable form.

2. A composition as claimed in claim 1, in which the source of said nervonic acid is the seed oil of *Lunaria biennis* or *Lunaria annua*.

3. A pharmaceutically composition for use in treatment of demyelinating diseases such as multiple sclerosis by oral ingestion, said composition comprising nervonic acid (cis-tetracos-15-acid) in a physiologically acceptable form, and an additional long-chain fatty acid (C16 to C26) in a physiologically acceptable form.

4. A composition as claimed in claim 3, wherein said nevonic acid is present in the form of a triglyceride.

5. A composition as claimed in claim 3, wherein said additional long-chain fatty acid (C16 to C26) is in the form of its ester.

6. A composition as claimed in claim 5, wherein said ester is a triglyceride ester.

7. A composition as claimed in claim 3, wherein said nervonic acid comprises at least 20% by weight of the therapeutically active component of said composition.

8. A process for treating a host having a demyelinating disease such as multiple sclerosis and in need of treatment for the symptoms thereof, comprising administering a pharmacologically effective amount of a composition including nervonic acid in a physiologically acceptable form to ameliorate the symptoms of said disease.

9. A process as claimed in claim 8, in which the source of said nervonic acid is the purified seed oil of *Lunaria biennis* or *Lunaria annua*.

10. A process as claimed in claim 8, in which said nervonic acid is in the form of an ester thereof.

11. A process as claimed in claim 8, in which said nervonic acid is in the form of its triglyceride ester.

12. A process as claimed in claim 8, in which said composition further includes an additional long-chain fatty acid (C16 to C26) in a physiologically acceptable form.

13. A process as claimed in claim 8, in which said additional long-chain fatty acid is present in the form of an ester thereof.

14. A process as claimed in claim 13, in which said ester of said additional long-chain fatty acid is a triglyceride ester.

* * * * *